(12) United States Patent
Takami

(10) Patent No.: US 7,525,320 B2
(45) Date of Patent: Apr. 28, 2009

(54) VOLTAGE CONTROL CIRCUIT FOR ENDOSCOPE

(75) Inventor: Satoshi Takami, Saitama (JP)

(73) Assignee: Hoya Corporation, Tokyo (JP)

( * ) Notice: Subject to any disclaimer, the term of this patent is extended or adjusted under 35 U.S.C. 154(b) by 259 days.

(21) Appl. No.: 11/393,871

(22) Filed: Mar. 31, 2006

(65) Prior Publication Data
US 2006/0232667 A1 Oct. 19, 2006

(30) Foreign Application Priority Data
Apr. 14, 2005 (JP) .......................... P2005-117005

(51) Int. Cl.
- H01H 31/02 (2006.01)
- H04N 13/00 (2006.01)
- A61B 1/04 (2006.01)

(52) U.S. Cl. .......................... 324/555; 348/45; 600/118

(58) Field of Classification Search ................. 324/555, 324/500; 348/42, 45, 65, 72; 600/101, 118
See application file for complete search history.

(56) References Cited

U.S. PATENT DOCUMENTS

| | | | |
|---|---|---|---|
| 5,610,967 A * | 3/1997 | Moorman et al. ........... 378/154 |
| 6,169,406 B1 * | 1/2001 | Peschel ....................... 324/548 |
| 6,449,577 B1 * | 9/2002 | Timpe ......................... 702/118 |
| 6,494,827 B1 * | 12/2002 | Matsumoto et al. ......... 600/118 |
| 6,686,949 B2 * | 2/2004 | Kobayashi et al. ............ 348/65 |
| 6,707,485 B1 * | 3/2004 | Higuchi et al. ................ 348/69 |
| 6,980,227 B2 | 12/2005 | Iida et al. |
| 7,206,343 B2 * | 4/2007 | Pearce ........................ 375/238 |
| 2004/0021449 A1 * | 2/2004 | Stenestam et al. ........... 323/255 |

FOREIGN PATENT DOCUMENTS

JP 3315809 6/2002

\* cited by examiner

Primary Examiner—Vincent Q Nguyen
Assistant Examiner—Hoai-An D Nguyen
(74) Attorney, Agent, or Firm—Greenblum & Bernstein, P.L.C.

(57) ABSTRACT

A voltage control circuit includes a voltage step-up device that steps up an applied voltage to a stepped-up voltage, an electronic device to which the stepped-up voltage is applied, a current monitor that monitors a supplied current that is supplied to the electronic device, based on the stepped-up voltage, a step-up controller that controls the stepped-up voltage to be a predetermined target voltage, based on the supplied current, and a warning provider that provides a warning when the current monitor can not monitor the supplied current.

8 Claims, 13 Drawing Sheets

VOLTAGE CONTROL CIRCUIT FOR ENDOSCOPE

BACKGROUND OF THE INVENTION

1. Field of the Invention

The present invention relates to a voltage control circuit for an endoscope, and especially relates to a voltage control circuit including a voltage step-up circuit for a light source for illuminating a subject, and so on.

2. Description of the Related Art

A light source for illuminating a subject is sometimes provide at a tip of a scope of an endoscope, for observing a dark subject inside a body. As a light source, an LED is known. In the case where a battery for driving the light source is used, a voltage step-up circuit is also generally used. This is because a high voltage is required for stabilizing the current supplied to an LED especially if the battery voltage has changed, or for increasing the current supplied to the LED for increasing brightness of the illuminating light. Further, the amount of current supplied to the LED for illumination is controlled by monitoring and feeding back the current.

Generally, in the case where an LED for illumination is provided at the tip of a scope of a portable endoscope, the voltage control circuit for the voltage step-up circuit is located apart from the LED. When a portable endoscope is manufactured, each of the voltage control circuit and the LED is built separately, and after being built, they are connected to each other. Therefore, a disconnection between the circuit and the LED, such as a soldering error on lead wires, may occur. Further, the tip of a scope is required to be small and the space for installing the LED is small, therefore, a connecting error when installing the LED may also occur.

When an error occurs with the LED for illuminating a subject, such as a disconnection error, feeding back the current becomes impossible and the step up circuit becomes uncontrollable. Therefore, a large excess voltage being much higher than the required level, may be generated. In this case, peripheral elements may be broken when the excess voltage level is higher than the tolerance level of the elements.

SUMMARY OF THE INVENTION

Therefore, an object of the present invention is to provide a voltage control circuit that can provide a warning on a display to inform of an error and identify the cause of the error to a user, when a step-up circuit becomes uncontrollable.

A voltage control circuit according to the present invention, includes a voltage step-up device that steps up an applied voltage to a stepped-up voltage, an electronic device to which the stepped-up voltage is applied, a current monitor that monitors a supplied current that is supplied to the electronic device, based on the stepped-up voltage, a step-up controller that controls the stepped-up voltage to be a predetermined target voltage, based on the supplied current, and a warning provider that provides a warning when the current monitor can not monitor the supplied current.

An endoscope according to the present invention, includes a voltage step-up device that steps up an applied voltage to a stepped-up voltage, an electronic device to which the stepped-up voltage is applied, a current monitor that monitors a supplied current that is supplied to the electronic device, based on the stepped-up voltage, a step-up controller that controls the stepped-up voltage to be a predetermined target voltage, based on the supplied current, and a warning provider that provides a warning when the current monitor can not monitor the supplied current.

BRIEF DESCRIPTION OF THE DRAWINGS

The present invention will be better understood from the description of the preferred embodiments of the invention set forth below together with the accompanying drawings, in which.

DESCRIPTION OF THE PREFERRED EMBODIMENTS

Hereinafter, the preferred embodiments of the present invention are described with reference to the attached drawings.

Figure 1:
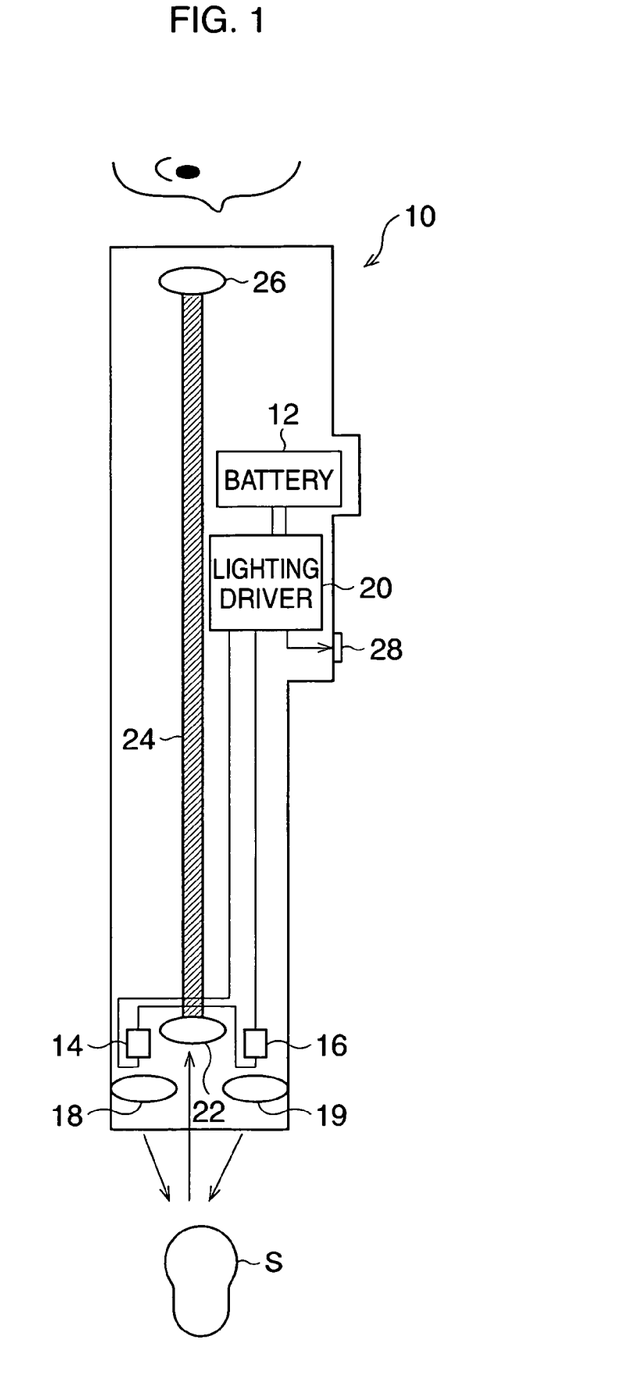
FIG. 1 is a block diagram of a fiber scope of a portable endoscope of the first embodiment.

As shown in FIG. 1, at the tip of a fiber scope 10, first and second LEDs 14 and 16 for illuminating a subject S, and first and second lighting lenses 18 and 19 are provided. The first and second LEDs 14 and 16 emit illuminating light on the subject S when provided with power from a battery 12, under the control of a light driving circuit 20. Illuminating light reflected from the surface of the subject S as reflected light, enters the eyes of a user via an objective lens 22, an imaging guide 24, and an eyepiece lens 26. The subject S is observed by a user.

A voltage-warning light 28 is provided on the surface of the body of the fiber scope 10 that a user holds. A voltage-warning LED (not shown) is included in the voltage-warning light 28. The voltage-warning LED emits light to inform a user of trouble occurring in the control process for stepping up the applied voltage from the battery 12, in the light driving circuit 20. For example, when it is impossible to carry out the control process for stepping up the applied voltage from the battery 12 due to a disconnection at the first LED 14 or the second LED 16 which should be connected to the light driving circuit 20, so that the applied voltage is stepped up by an abnormally large amount, the voltage-warning LED automatically emits light.

Figure 2:
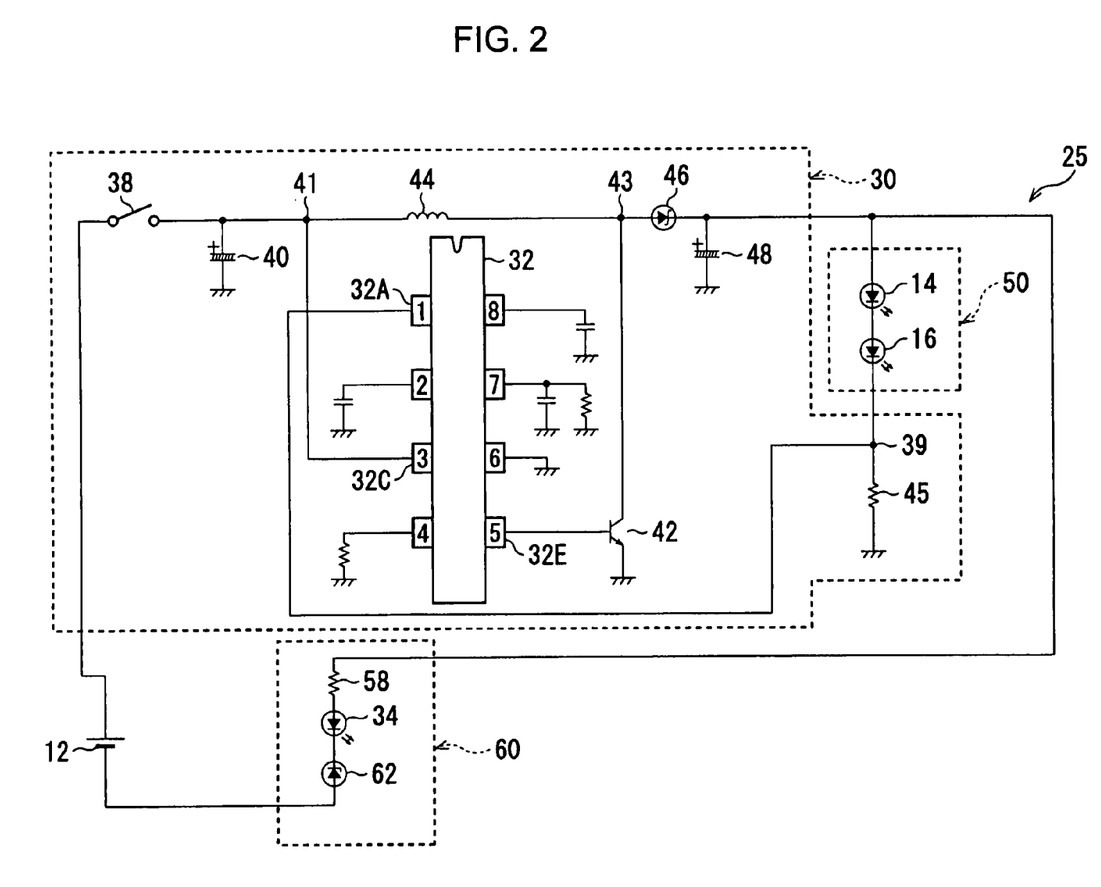
FIG. 2 is a block diagram of a voltage control circuit provided in a light driving circuit of the first embodiment.

As shown in FIG. 2, in the light driving circuit 20, a voltage control circuit 25 including a power-source control circuit 30, illuminating elements 50, and an auxiliary voltage-control circuit 60, are provided. In the power-source control circuit 30, a DC/DC converter and a power switch 38 are provided. The DC/DC converter includes the step-up DC/DC converter IC 32, a capacitor 40, a transistor 42, a coil 44, a first resistor 45, a shottky diode 46, and a smoothing capacitor 48. In the illuminating elements 50, the first and second LEDs 14 and 16 are provided.

When the applied voltage from the battery 12 is stepped up to the stepped-up voltage by the DC/DC converter and the stepped-up voltage is applied to the first and second LEDs 14 and 16, current flows to the first and second LEDs 14 and 16, so that the first and second LEDs 14 and 16 illuminate light. The current is monitored by the first resistor 45 which is connected to a first articulation point 39, and the DC/DC converter IC 32 operates so that a constant current flows to the first articulation point 39.

That is, when the power switch 38 is turned on, a voltage is applied to a third terminal 32C of the DC/DC converter IC 32 via a second articulation point 41. The DC/DC converter IC 32 supplies a pulse base current to the transistor 42 connected to a fifth terminal 32E of the DC/DC converter IC 32. The repeating frequency of the active period of the driving voltage which is applied to the transistor 42 by the DC/DC converter IC 32 via the fifth terminal 32E, that is, the repeating frequency at the fifth terminal being in a high state, is changeable according to the voltage at the first articulation point 39, detected by the first terminal 32A.

That is, when the voltage at the first articulation point 39 is lower than a set voltage, the repeating frequency of the voltage from the fifth terminal 32E at the base terminal of the transistor 42, being in a high state is shortened, so that the frequency of the transistor 42 being in an on state, becomes high. On the other hand, when the voltage at the first articulation point 39 is higher than a set voltage, the repeating frequency of the voltage from the fifth terminal 32E at the base terminal of the transistor 42, being in a high state is lengthened, so that the frequency of the transistor 42 being in an on state becomes low. As a result of this, the voltage at the first articulation point 39, that is, the stepped-up voltage applied to the first and second LEDs 14 and 16 is kept at almost a constant voltage (target voltage).

The coil 44 which functions as a step up inductor is provided between the second articulation point 41 and the third articulation point 43, the shottky diode 46 is provided between the third articulation point 43 and the first LED 14, to prevent reverse current, and the smoothing capacitor 48 is provided to smooth the current.

In the auxiliary voltage-control circuit 60, the voltage-warning LED 34, a second resistor 58, and a zener diode 62 are provided in case the stepping up process is not properly controlled due to trouble with the DC/DC converter and so on. For example, when a disconnection occurs at the first LED 14 or the second LED 16, current to the first resistor 45 stops flowing, and the voltage at the first articulation point 39 becomes undetectable by the first terminal 32A, so that the voltage applied by the DC/DC converter IC 32 may become abnormally high. Therefore, in a voltage control circuit where an auxiliary voltage-control function is not provided, such as a comparative circuit explained later, a higher voltage than the target voltage (hereinafter an excess voltage) is output from the power-source control circuit 30, and each element may be broken.

On the other hand, in the auxiliary voltage-control circuit 60 having the zener diode 62, the excess voltage is applied to the zener diode 62 via the second resistor 58. When the excess voltage being higher than the predetermined zener voltage is applied to the zener diode 62, additional current is drawn from the output side of the power-source control circuit 30 and flows to the zener diode 62. That is, the additional current flows to the zener diode 62 from the output side of the power-source control circuit 30. As a result of this, generation of an excess voltage stepped up to be much higher than the zener voltage is prevented, and the voltage-warning LED 34 emits light.

Figure 3:
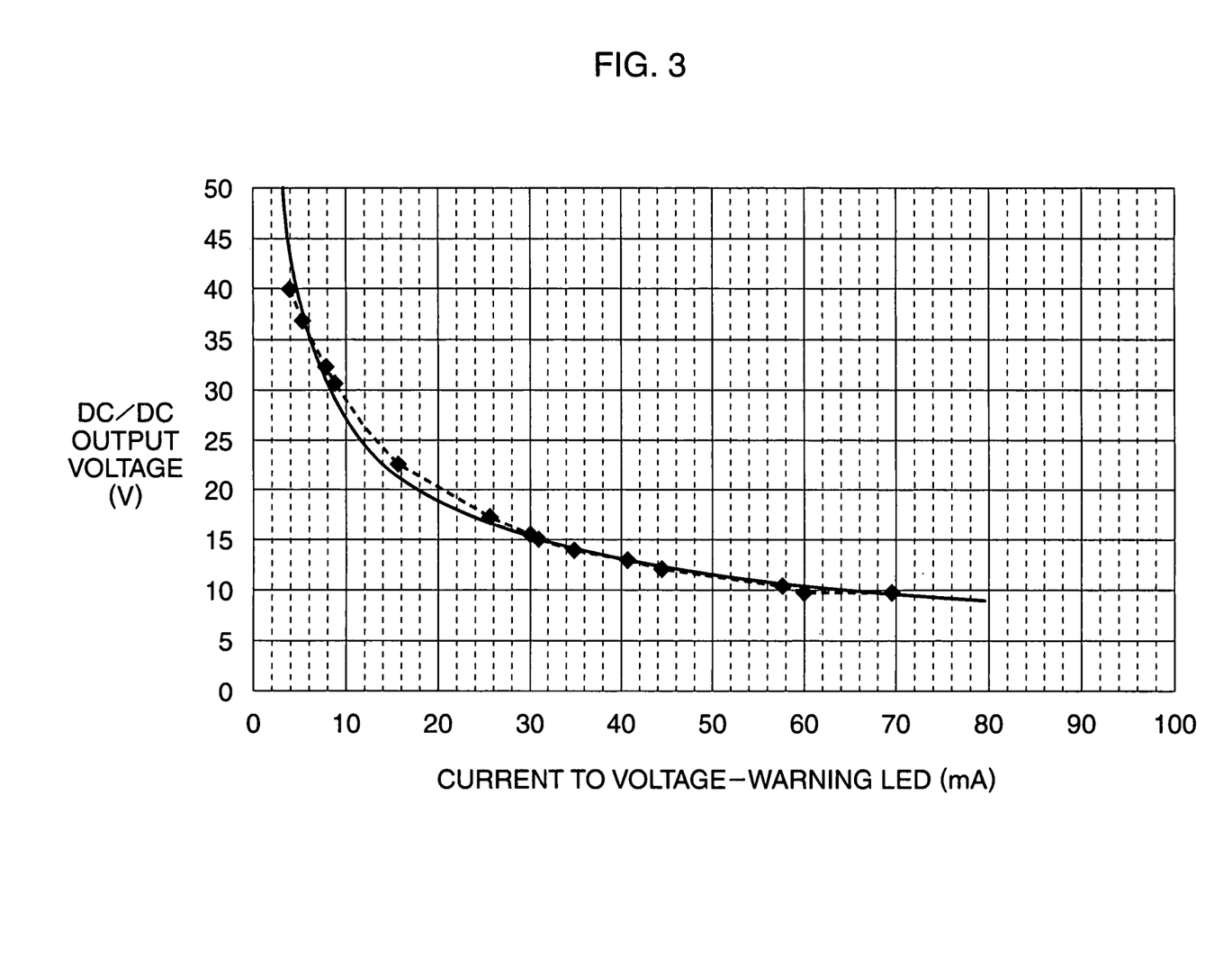
FIG. 3 is a graph representing a relation between the amount of current flowing to a voltage-warning LED and the amount of voltage output from a DC/DC converter.

FIG. 3 represents a relation between the amount of current flowing to the voltage-warning LED 34 and the amount of voltage output from the DC/DC converter, when a disconnection at the first LED 14 or the second LED 16 and so on occurs, the voltage at the first articulation point 39 becomes undetectable by the first terminal 32A.

The plurality of points plotted on the broken line in FIG. 3, represent measured values of the current flowing to the voltage-warning LED 34 and the output voltage from the DC/DC converter. The asymptotic curve (solid line) in FIG. 3 approaches these points smoothly. The amount of current flowing to the voltage-warning LED 34 is calculated by subtracting the zener voltage drop at the zener diode 62 and the forward voltage to the voltage-warning LED 34 from the output voltage of the DC/DC converter, and dividing the subtracted result by the resistance value of the second resistor 58.

The level of the output voltage from the DC/DC converter, is extremely large when only a small current flows to the voltage-warning LED 34, the second resistor 58, and the zener diode 62. However, when a slightly larger amount of current flows through these elements, the output voltage from the DC/DC converter drops by a large amount. That is, the second resistor 58 and the zener diode 62 prevent the generation of an excess voltage that is much larger than the target voltage.

As mentioned above, in the voltage control circuit 25 of this embodiment, in the case where the stepping up of voltage by the power-source control circuit 30 becomes uncontrollable, generation of excess voltage is prevented, and a user is informed of the trouble in the voltage stepping up control process when the voltage-warning LED 34 starts to emit light.

The voltage control circuit 25 of this embodiment, can be provided in fixed type endoscopes using a commercial power source, not only in the fiber scope 10 which is portable and uses the battery 12.

Figure 4:
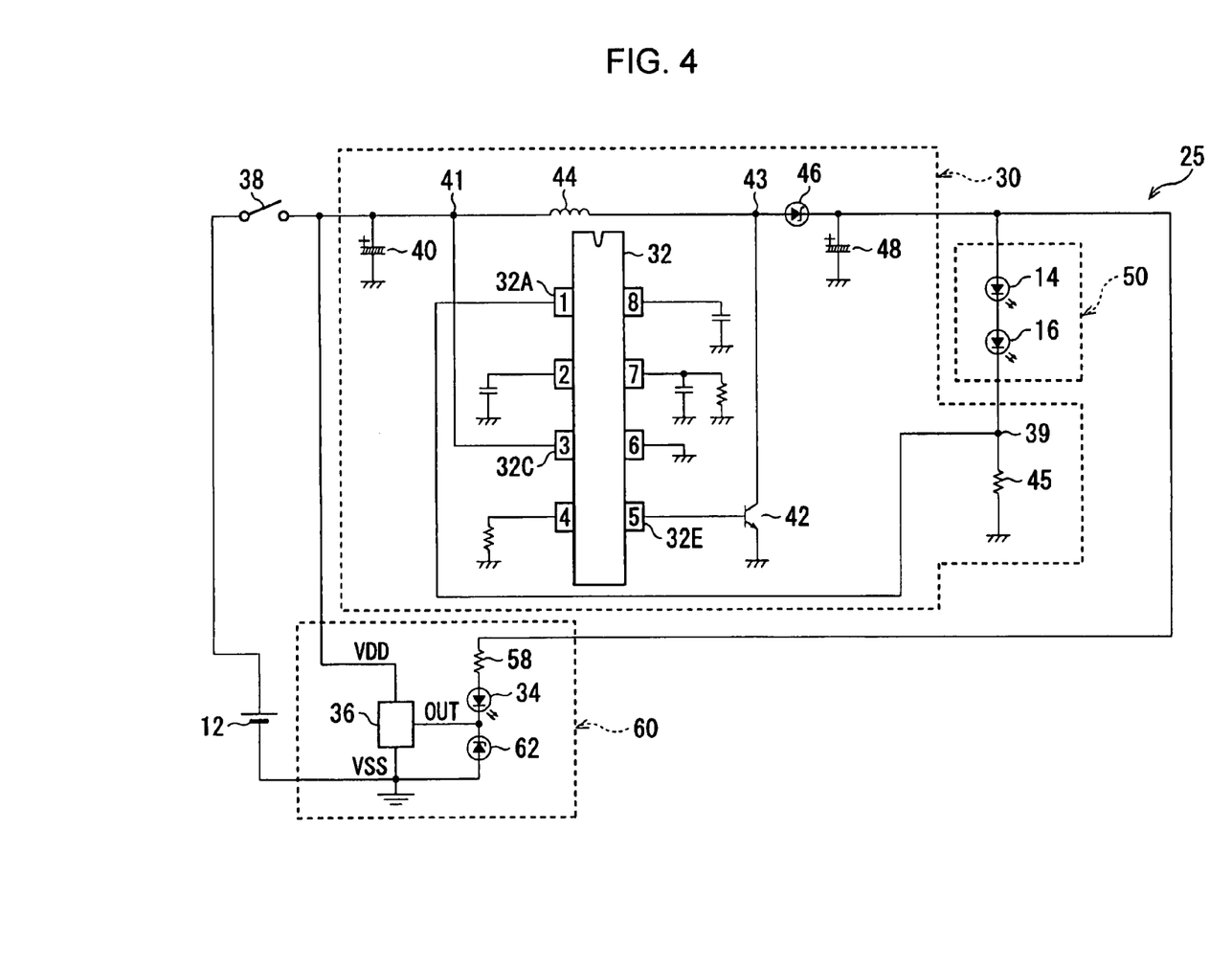
FIG. 4 is a block diagram of a voltage control circuit of the second embodiment.
Figure 5:
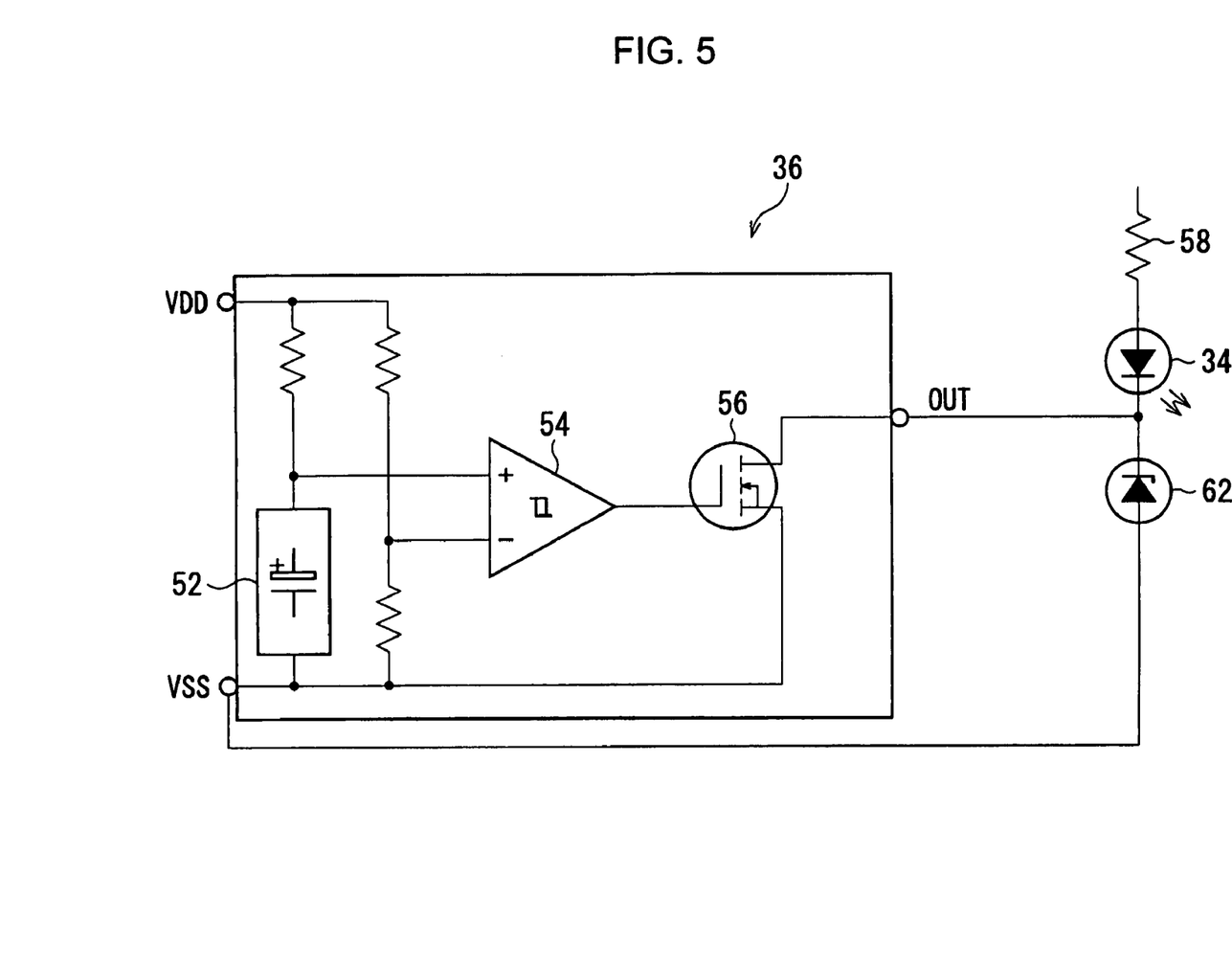
FIG. 5 is a block diagram of an auxiliary voltage-control circuit having a voltage warning display function.

Hereinafter, the second embodiment is explained. In FIGS. 4 and 5, showing the second embodiment, the components that are the same as those in the first embodiment have the same reference numerals as those in the first embodiment.

In the voltage control circuit 25 of the second embodiment, a voltage warning display function and a display driving circuit 36 are provided in the auxiliary voltage-control circuit 60, and this is the difference to the first embodiment. The display driving circuit 36 is provided to further make the voltage-warning LED 34 emit light when the applied voltage from the battery 12 has decreased due to long-term usage and so on, and for warning a user of the drop in the applied voltage.

Next, the operation of the display driving circuit 36 is explained (see FIG. 5). In the display driving circuit 36, a standard voltage generating circuit 52 is provided. The standard voltage generating circuit 52, for example, generates a standard voltage of 2.3 (V). The applied voltage input by the battery 12 is divided by resistors, and the divided voltage and the standard voltage are input to the comparator 54. In the comparator 54, these input voltages are compared and it is judged whether the applied voltage from the battery 12 is smaller than the standard voltage of 2.3 (V) or not.

When it is judged that the divided voltage according to the applied voltage from the battery 12 is smaller than the standard voltage, the high state voltage is applied to the gate of the n-channel FET 56 by the comparator 54. Therefore, when the divided voltage from the battery 12 is smaller than the standard voltage, the voltage at the output terminal of the comparator 54 becomes high, the gate voltage of the n-channel FET 56 also becomes high, and current flows between the drain and source. As a result of this, the current flows to the voltage-warning LED 34 connected to the n-channel FET 56 via the second resistor 58, and the voltage-warning LED 34 emits light to inform a user that the residual quantity of the battery 12 is smaller than the predetermined level.

As mentioned above, due to the auxiliary voltage-control circuit 60 having the voltage warning display function, the voltage-warning LED 34 emits light, not only when the output voltage from the DC/DC converter is large excess because control of the voltage stepping up process by the power-source control circuit 30 becomes impossible, similarly to the first embodiment, but also when the applied voltage from the battery 12 has decreased.

In this embodiment, when the output voltage of the battery 12 is decreased, as long as the power-source control circuit 30 functions, current is supplied to the voltage-warning LED 34 based on the stepped up voltage. That is, current based on the output voltage of the battery 12 is not supplied to the voltage-warning LED 34, but current based on voltage stepped up under the control of the power-source control circuit 30, is supplied via the second resistor 58.

As mentioned above, when the applied voltage from the battery 12 is decreased, sufficient current is supplied to the voltage-warning LED 34 to light it brightly, based on the stepped up voltage via the second resistor 58, as long as the power-source control circuit 30 operates. Therefore, the voltage-warning light 28 can clearly inform a user that the output voltage of the battery 12 has decreased. Note that in this embodiment, the DC/DC converter operates when a voltage higher than 2.0(V) is applied from the battery 12.

Figure 6:
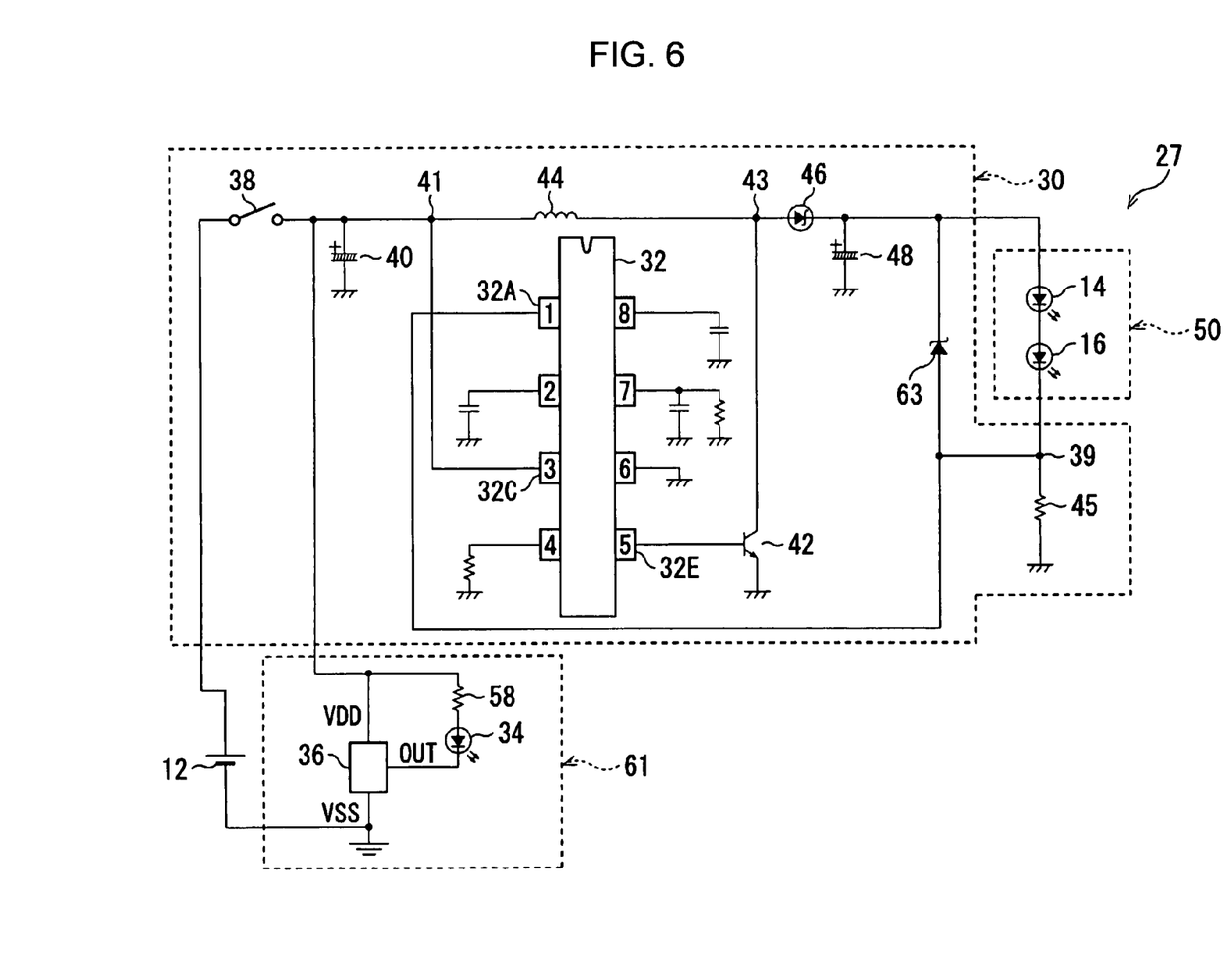
FIG. 6 is a block diagram of a voltage control circuit of a comparative example.

On the other hand, in a voltage control circuit 27 of a comparative example shown in FIG. 6, while the illuminating elements 50 are driven by the stepped up voltage generated by the power-source control circuit 30 from the applied voltage from the battery 12, the voltage-warning LED 34 is directly connected to the battery 12 via the second resister 58 and emits light using the current generated by the applied voltage from the battery 12 and the second resister 58. Therefore, brightness of the light emitted by the voltage-warning LED 34 decreases in accordance with the decreased residual quantity of the battery 12. As a result of this, when the voltage-warning LED 34 emits light to warn that the residual quantity of the battery 12 has decreased, the amount of the current flowing through the voltage-warning LED 34 is small. Therefore, brightness of the light emitted by the voltage-warning LED 34 is low, so that the warning display may not be recognized by a user.

Note that in the comparative example in FIG. 6, a zener diode 63 is provided between an output terminal at the hot side of the smoothing capacitor 48 and the first articulation point 39, as an excessive voltage protection circuit for protecting the power-source control circuit 30 from an excessive voltage generated by an open load due to the disconnection of the illuminating elements 50.

Figure 7:
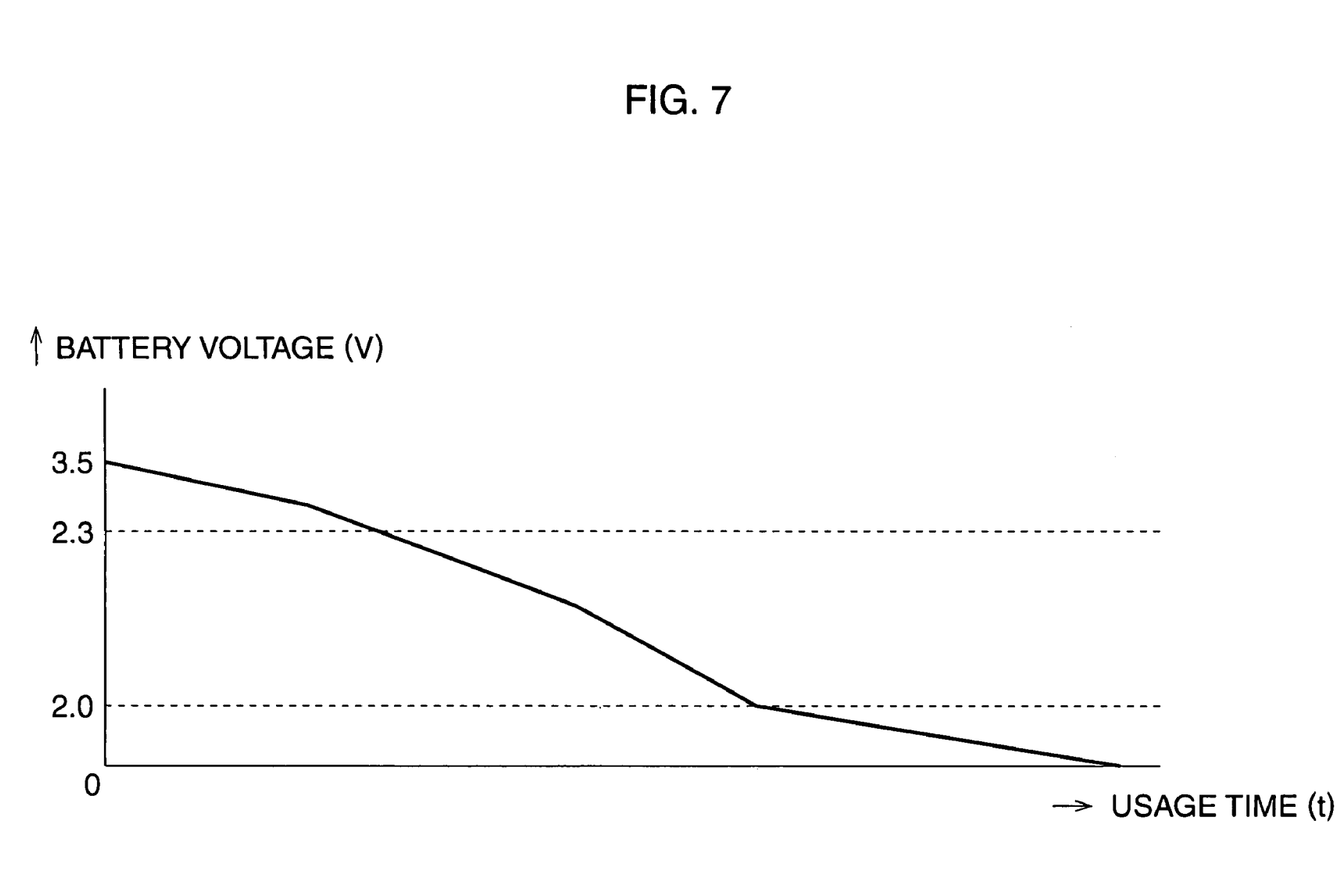
FIG. 7 is a graph representing the change in the applied voltage from a battery over time.
Figure 8:
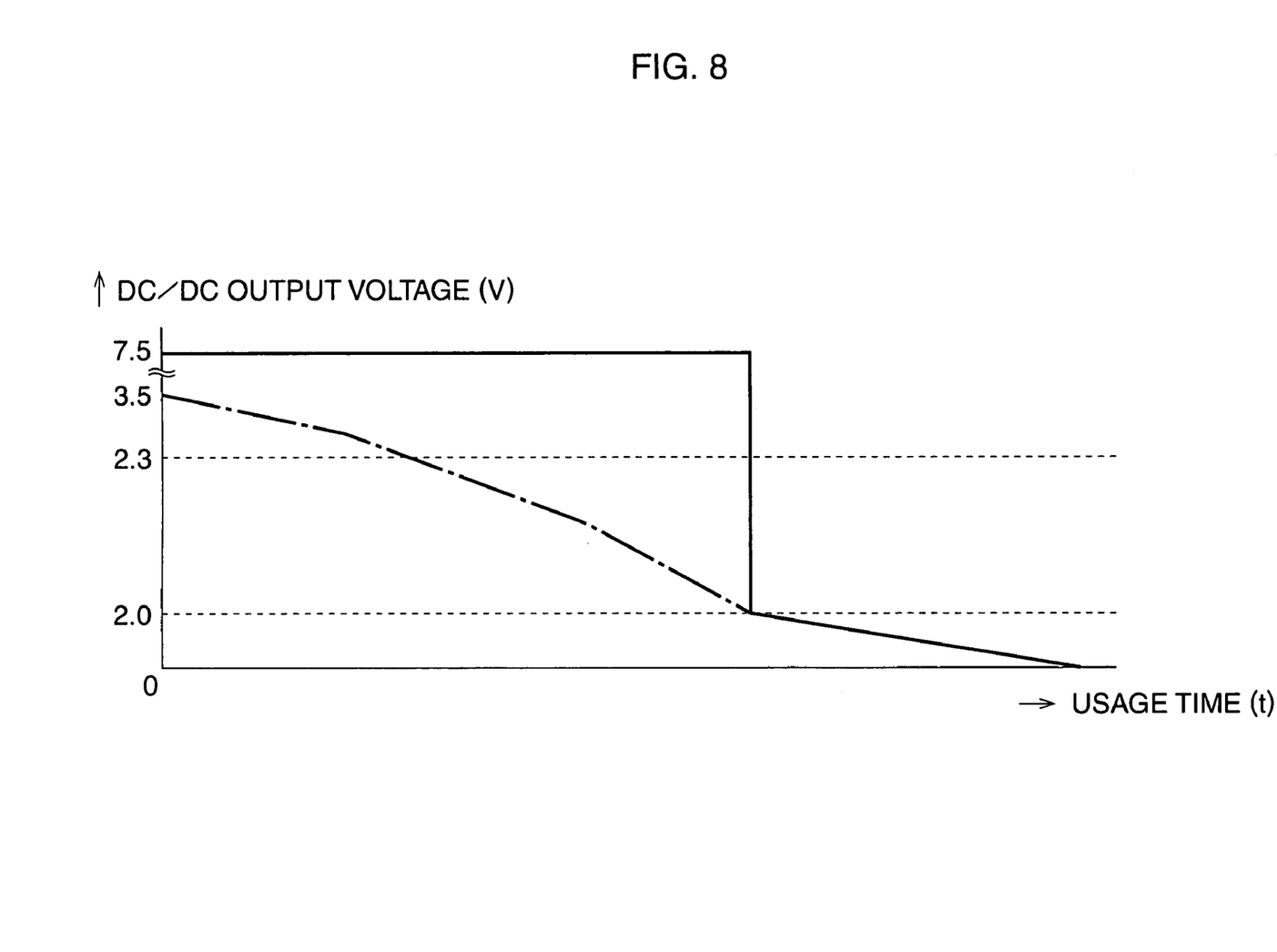
FIG. 8 is a graph representing the change in the output voltage from a power source control circuit over time.

As shown in FIG. 7, the applied voltage from the battery 12, that is battery voltage, is 3.5 (V) at the start of use (the usage time "t"=0), and gets smaller with the passing of usage time "t". In FIGS. 8-13, the situation where the applied voltage changes as shown in FIG. 7, is premised. When the applied voltage from the battery 12 is more than 2.0 (V), the DC/DC converter operates so that the output voltage from the DC/DC converter is constant, for example being 7.5 (V) (see FIG. 8). When the amount of the applied voltage becomes smaller than 2.0 (V), the DC/DC converter does not operate because a voltage larger than 2.0 (V) is necessary for the operation of the DC/DC converter IC 32. Therefore, applied voltage from the battery 12 is output via the coil 44, the shottky diode 46, and the second resistor 58. At this time, in the auxiliary voltage-control circuit 60 having the warning display function, the voltage-warning LED 34 is switched on for emitting light, and therefore the voltage-warning LED 34 emits light.

Figure 9:
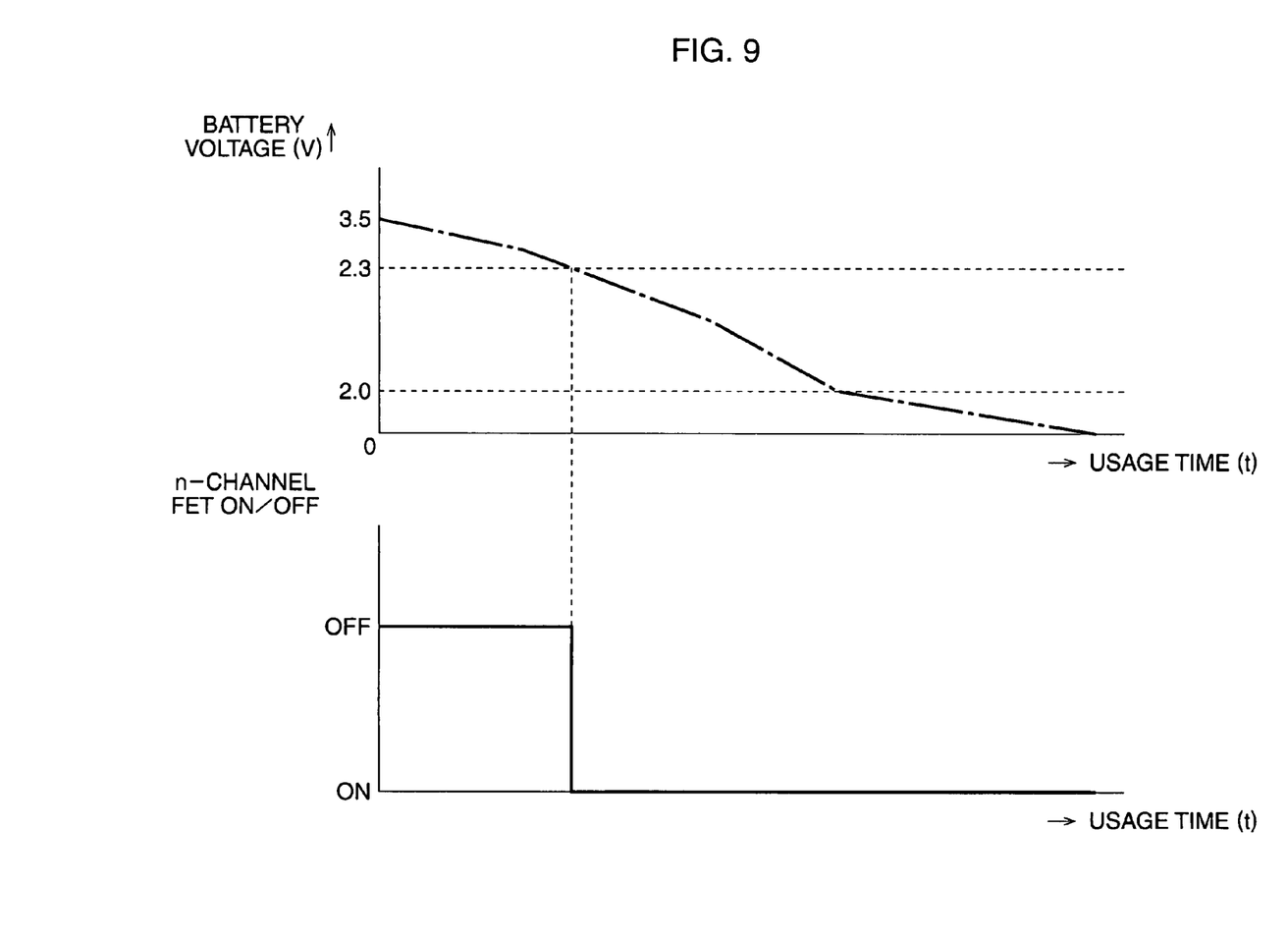
FIG. 9 is a graph representing an operation state of an n-channel FET in a display driving circuit.

When the applied voltage is lower than the standard voltage of 2.3 (V) and higher than 2.0 (V), because the DC/DC converter operates, the n-channel FET 56 in the display driving circuit 36 is turned to be in the on state (see FIG. 9). At this time, the output voltage at the output terminal "OUT" (see FIG. 5) is decreased similarly to the applied voltage from the battery 12. As a result of this, current corresponding to the decreased voltage is supplied to the voltage-warning LED 34, so that the voltage-warning LED 34 emits light. In accordance with the decrease in the applied voltage from the battery 12 represented by FIGS. 7 to 9, the change over time in brightness of light emitted by the voltage-warning LED 34, in the auxiliary voltage-control circuit 60 having the voltage warning display function, is explained below.

Figure 10:
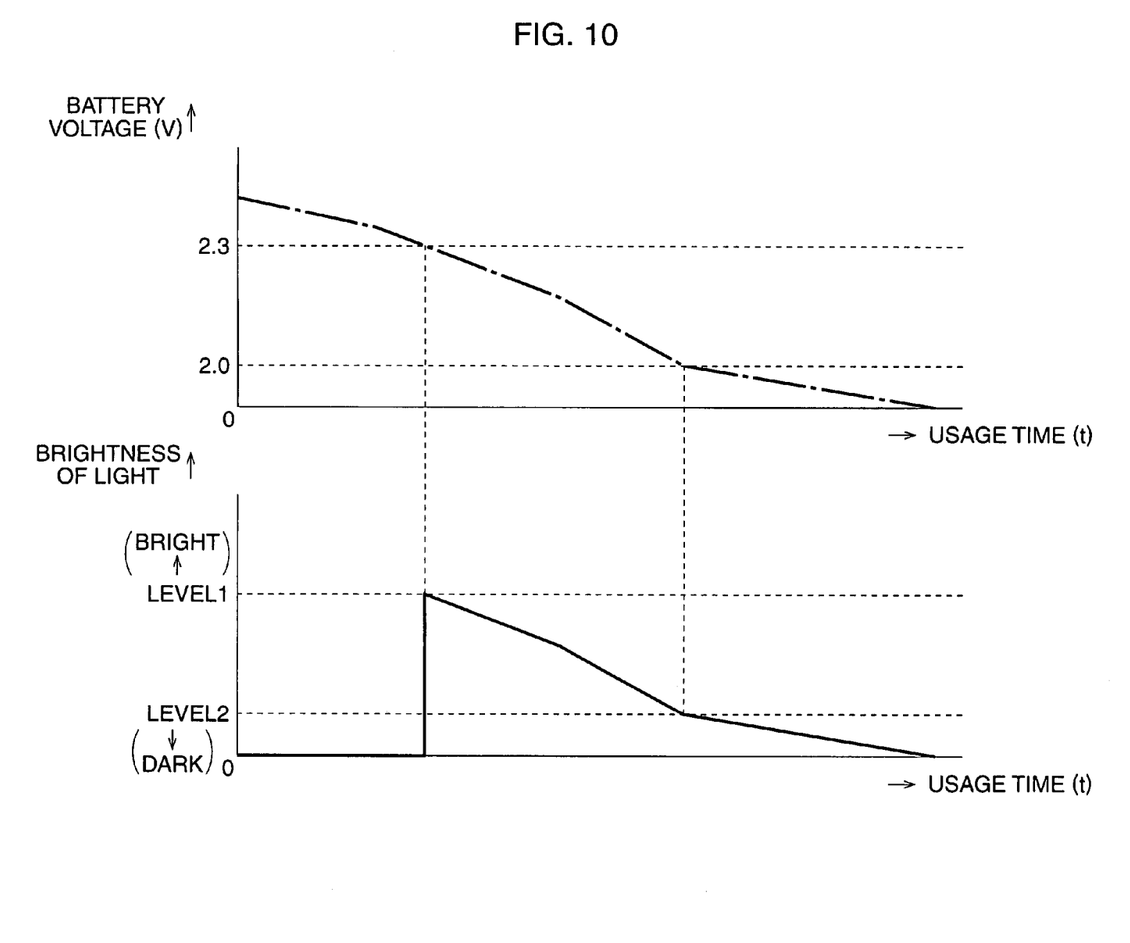
FIG. 10 is a graph representing the change in brightness of light emitted by the voltage-warning LED of the comparative example in FIG. 6.
Figure 11:
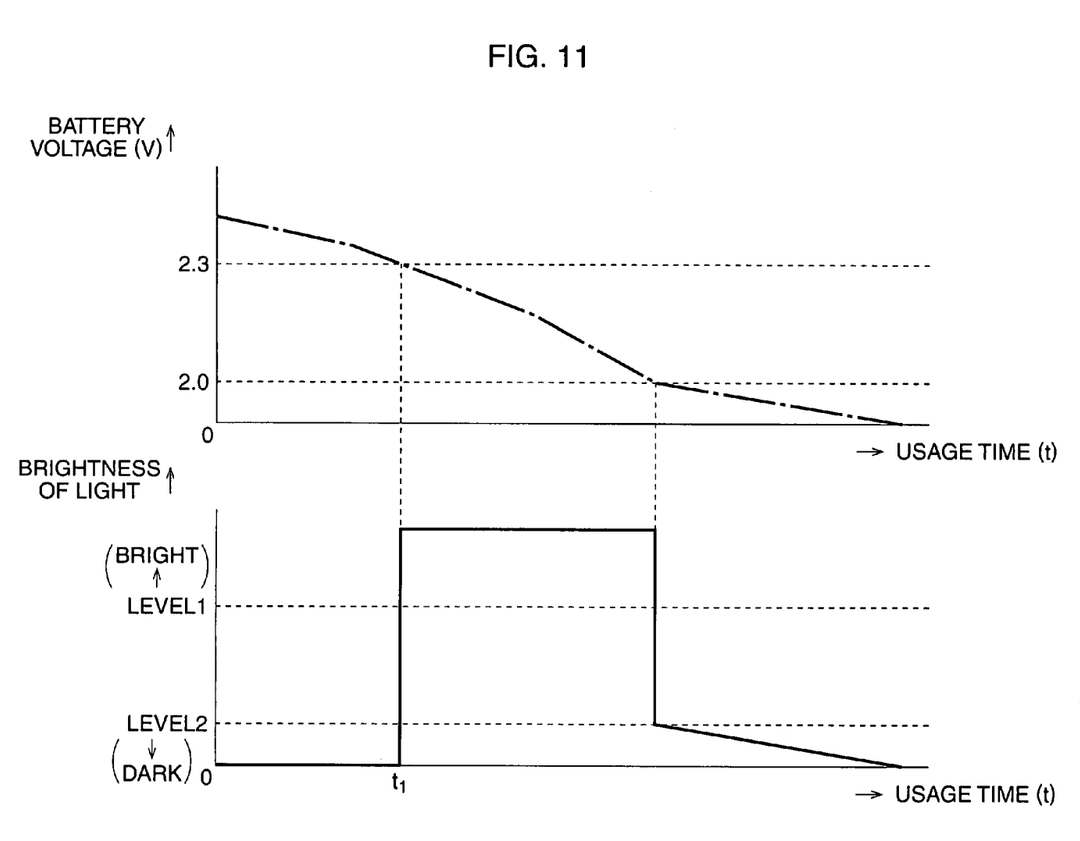
FIG. 11 is a graph representing the change in brightness of light emitted by the voltage-warning LED in the auxiliary voltage-control circuit.

Both in FIG. 10 representing the change in brightness of light emitted by the voltage-warning LED 34 directly using the power from the battery 12, in a display circuit 61 of the comparative example (see FIG. 6), and in FIG. 11 representing the change in brightness of light emitted by the voltage-warning LED 34 in the auxiliary voltage-control circuit 60, the chain line represents the change over time in the applied voltage from the battery 12. When the applied voltage from the battery 12 is higher than the standard voltage of 2.3 (V), both in the display circuit 61 of the comparative example and in the auxiliary voltage-control circuit 60, the voltage-warning LED 34 does not light. When the applied voltage gradually decreases, and becomes lower than the standard voltage of 2.3(V), in the display circuit 61, brightness of light emitted by the voltage-warning LED 34 also gradually decreases from brightness level in proportion to the standard voltage of 2.3 (V) (hereinafter, level 1). This is because the current flowing to the voltage-warning LED 34, that depends on the applied voltage from the battery 12 decreases.

On the other hand, a stable voltage that is in proportion to the output voltage from the DC/DC converter and much higher than the standard voltage of 2.3 (V) is applied to the voltage-warning LED 34 in the auxiliary voltage-control circuit 60 having the voltage warning display function. Therefore, a large current can constantly be supplied, so that the voltage-warning LED 34 can emit light having a constant brightness level (see FIG. 11).

When the applied voltage from the battery 12 drops below 2.0 (V), the stepped-up voltage from the DC/DC converter stops, in both the auxiliary voltage-control circuit 60 having the voltage warning display function, and in the display circuit 61, because the DC/DC converter does not operate.

Therefore, brightness of light emitted by the voltage-warning LED 34 is at a level that is in proportion to the applied voltage 2.0 (V) through the coil 44, the shottky diode 46, the second resistor 58, and so on (hereinafter, level 2). When the applied voltage from the battery 12 is further reduced and drops under 2.0 (V), brightness of light from the voltage-warning LED 34 also drops to a level below level 2, in accordance with the applied voltage.

As mentioned above, brightness of light emitted by the voltage-warning LED 34 in the display circuit 61 of the comparative example, becomes lower than level 1 to less than level 2, regardless of whether the DC/DC converter operates or not. On the other hand, brightness of light emitted by the voltage-warning LED 34 in the auxiliary voltage-control circuit 60 having the voltage warning display function, is much higher than level 1 until the end of the operation of the DC/DC converter.

In this embodiment, as mentioned above, the voltage-warning LED 34 emits a bright light until just before the DC/DC converter stops operation, that is until the requirement for warning of a drop in the applied voltage from the battery 12 is the largest, so that the voltage-warning light 28 including the voltage-warning LED 34 can clearly inform a user of a decrease in the residual quantity of the battery 12.

In this embodiment, the DC/DC converter operates when a voltage higher than 2.0(V) is applied, therefore, the standard voltage is set to be 2.3 (V) which is slightly higher than 2.0(V). The level of the standard voltage can be modified according to the minimum required level of the applied voltage for the operation of the DC/DC converter and other circuits, which operate for stepping up voltage.

Figure 12:
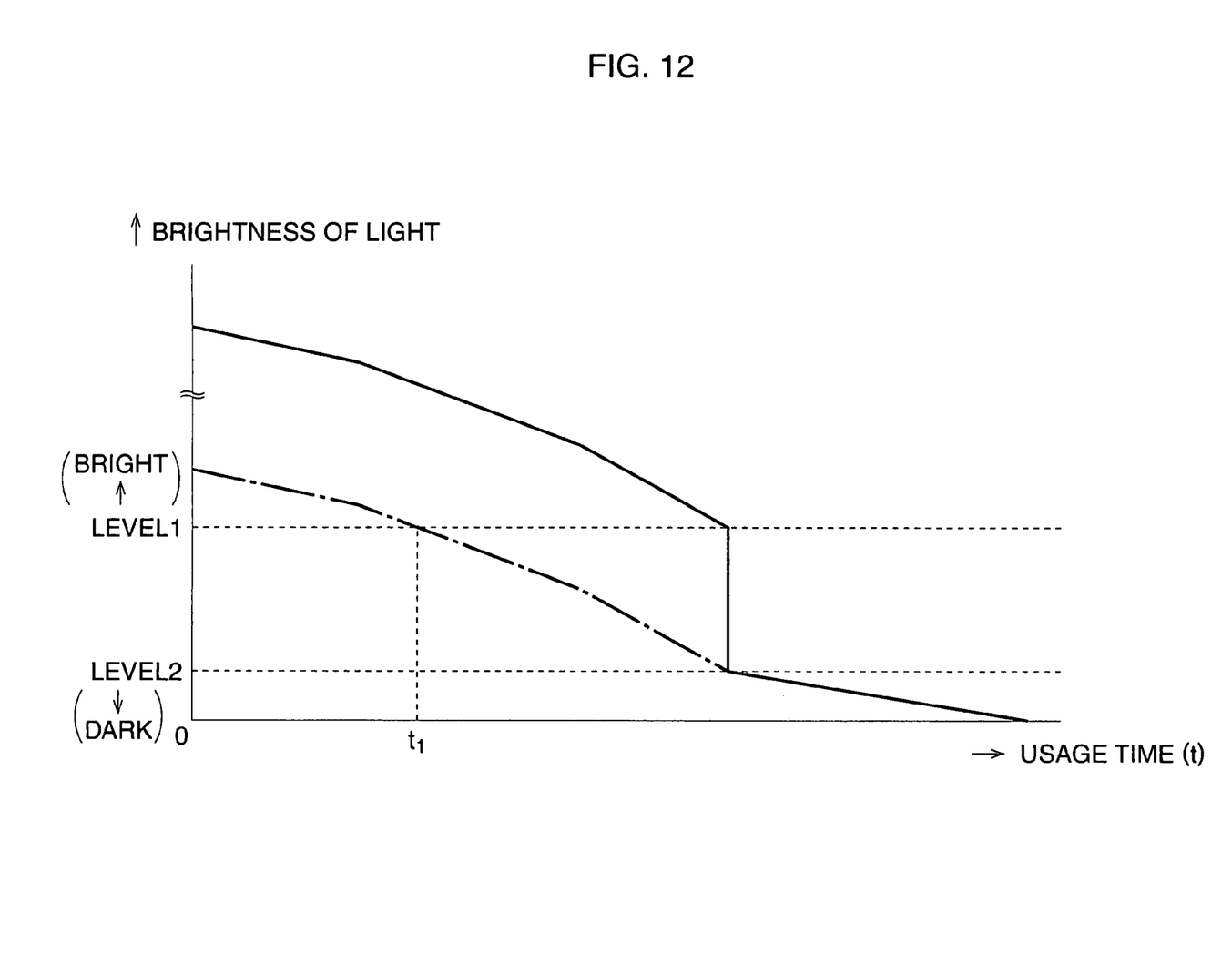
FIG. 12 is a graph representing the change in brightness of light emitted by the voltage-warning LED due to trouble in the voltage stepping up control process and a decrease in the applied voltage.

In FIG. 12, when the applied voltage from the battery 12 represented by the chain line is higher than 2.3 (V), that is when the usage time "t"=0 to $t_1$, the voltage-warning LED 34 emits light only when trouble occurs in the voltage step up control process. In this case, brightness of light emitted by the voltage-warning LED 34 is higher than that when the applied voltage is lower than 2.3 (V), that is when the usage time "t">$t_1$. This is because current based on excess voltage larger than the voltage appropriately stepped up, temporally flows to the voltage-warning LED 34 when the applied voltage is not appropriately stepped up by the DC/DC converter IC 32 and so on.

As mentioned above, in this embodiment, the voltage-warning light 28 can clearly warn a user not only of trouble in the control process for stepping up the voltage due to an open load in the illuminating elements 50 and so on, but also of a drop in the applied voltage from the battery 12. Further, the structure of the auxiliary voltage-control circuit 60 can be simplified, because only the voltage-warning LED 34 as a single lighting element is provided for informing of trouble caused by a problem in the stepping up control process and a drop in the applied voltage from the battery 12.

In this embodiment, only the voltage-warning LED 34 is provided to inform of trouble in a control process for stepping up voltage, and a drop in the applied voltage, however, a plurality of lighting elements can be provided for informing of each respective problem. In this case, it is possible to inform a user which one of the voltage stepping up control process and the applied voltage drop, is the problem.

Figure 13:
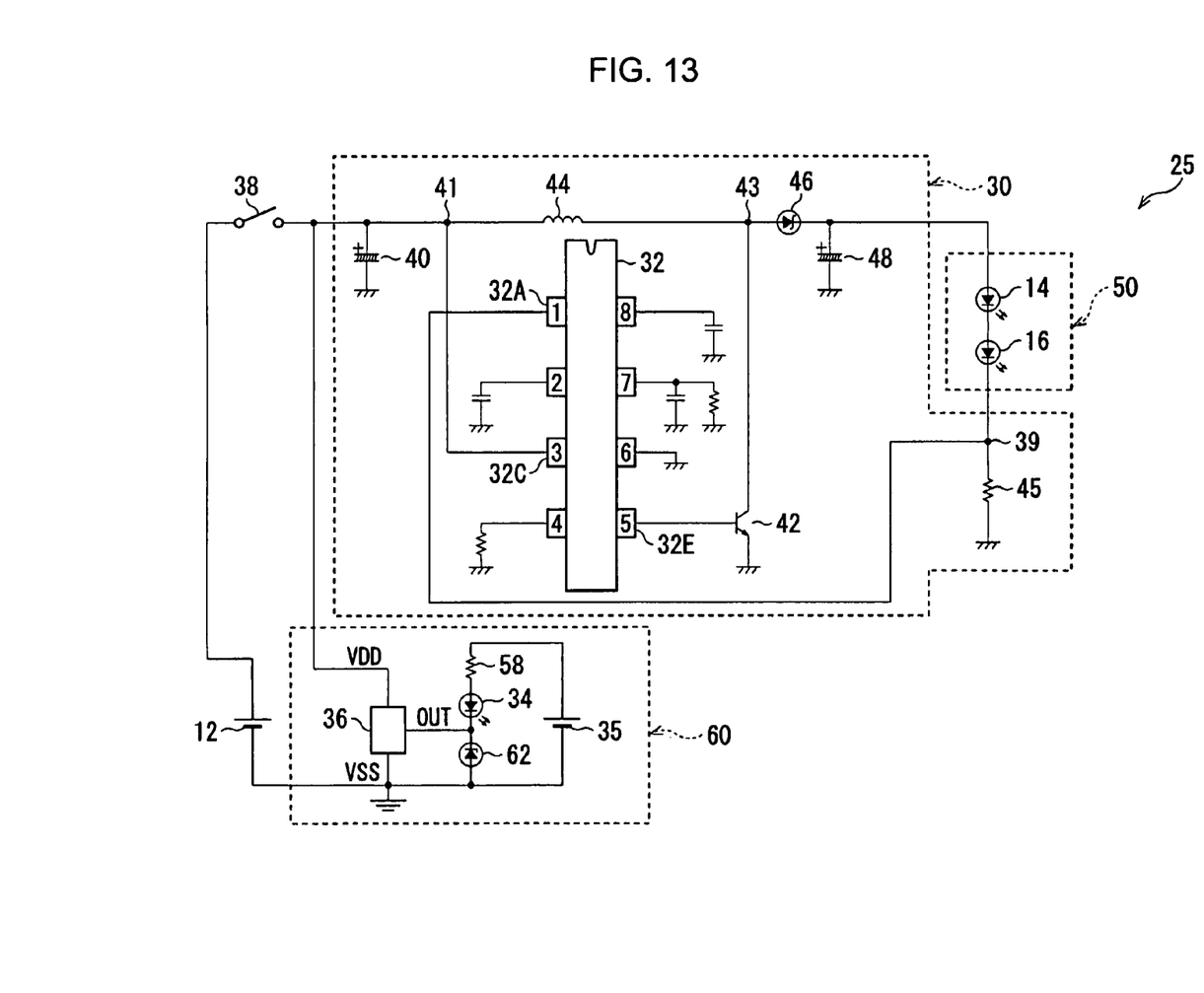
FIG. 13 is a block diagram of a voltage control circuit including an exclusive power source for the voltage-warning LED.

In this embodiment, as shown in FIG. 13, an additional power source 35 for indication, that is an exclusive power source for the voltage-warning LED 34 to indicate a drop in the battery voltage, can be installed. In this case, when the applied voltage from the battery 12 becomes lower than 2.0 (V) and the DC/DC converter IC 32 does not operate, brightness of light emitted by the voltage-warning LED 34 is maintained to be higher than the above-mentioned level 1.

In both the first and second embodiments, a lamp can be used instead of the first and second LED 14 and 16, being light sources for illuminating a subject, or the voltage-warning LED 34. Further, the number, arrangement, and so on of the light sources are not limited to those in the embodiments, for example, a single light source which emits bright light for illuminating a subject can be used, or two light sources can be arranged in parallel.

The voltage control circuit 25 can be produced using conventional elements. For example, the DC/DC converter IC 32 can be the "TK11840L" produced by TOKO, INC.

Finally, it will be understood by those skilled in the art that the foregoing description is of preferred embodiments of the apparatus, and that various changes and modifications may be made to the present invention without departing from scope thereof.

The present disclosure relates to subject matter contained in Japanese Patent Application No.2005-117005 (filed on Apr. 14, 2005) which is expressly incorporated herein, by reference, in its entirety.

The invention claimed is:

1. A voltage control circuit, comprising:
   a voltage step-up device that steps up an applied voltage to a stepped-up voltage;
   an electronic device to which said stepped-up voltage is applied;
   a current monitor that monitors a supplied current that is supplied to said electronic device, based on said stepped-up voltage;
   a step-up controller that controls said stepped-up voltage to be a predetermined target voltage, based on said supplied current; and
   a warning provider that provides a warning when said current monitor can not monitor said supplied current,
   wherein said step-up controller controls said stepped-up voltage not to be larger than said target voltage, when said current monitor can not monitor said supplied current, and
   wherein said step-up controller comprises a current drawer that is connected to an output side of said voltage step-up device and draws additional current from said output side of said voltage step-up device when said stepped-up voltage is larger than a predetermined voltage, so that said stepped-up voltage is controlled not to be larger than said target voltage.

2. The voltage control circuit according to claim 1, wherein said voltage step-up device comprises a step-up type DC/DC converter.

3. The voltage control circuit according to claim 1, wherein said current drawer comprises a zener diode and said predetermined voltage is a zener voltage of said zener diode.

4. The voltage control circuit according to claim 1, wherein said electronic device comprises an illuminating element which illuminates light when said supplied current is supplied, and said current monitor can not monitor said supplied current when a disconnection occurs in said illuminating element.

5. The voltage control circuit according to claim 1, wherein said warning provider comprises a light emitting element that emits light when said supplied current can not be monitored by said current monitor.

6. The voltage control circuit according to claim 5, wherein said light emitting element comprises an LED.

7. The voltage control circuit according to claim 1, further comprising:
a voltage judge that judges whether said applied voltage, that is provided from a battery to said voltage step-up device, is smaller than a standard voltage or not, wherein said warning provider provides a warning when said voltage judge judges that said applied voltage is smaller than said standard voltage.

8. An endoscope, comprising:
a voltage step-up device that steps up an applied voltage to a stepped-up voltage;
an electronic device to which said stepped-up voltage is applied;
a current monitor that monitors a supplied current that is supplied to said electronic device, based on said stepped-up voltage;
a step-up controller that controls said stepped-up voltage to be a predetermined target voltage, based on said supplied current; and
a warning provider that provides a warning when said current monitor can not monitor said supplied current,
wherein said electronic device comprises an illuminating element which illuminates light when said supplied current is supplied, and said current monitor can not monitor said supplied current when a disconnection occurs in said illuminating element.

* * * * *